United States Patent [19]
Turick et al.

[11] Patent Number: 5,681,739
[45] Date of Patent: Oct. 28, 1997

[54] METHOD FOR IN SITU OR EX SITU BIOREMEDIATION OF HEXAVALENT CHROMIUM CONTAMINATED SOILS AND/OR GROUNDWATER

[75] Inventors: Charles E. Turick; William W. Apel, both of Idaho Falls, Id.

[73] Assignee: Lockheed Idaho Technologies Company, Idaho Falls, Id.

[21] Appl. No.: 452,591

[22] Filed: May 25, 1995

[51] Int. Cl.$^6$ .................................................. C12N 1/20
[52] U.S. Cl. .............................. 435/262.5; 435/253
[58] Field of Search ............................. 435/262.5, 253

[56] References Cited

U.S. PATENT DOCUMENTS

| | | | |
|---|---|---|---|
| 3,941,691 | 3/1976 | Romanenko et al. | 210/2 |
| 4,468,461 | 8/1984 | Bopp | 435/253 |
| 4,522,723 | 6/1985 | Kauffman et al. | 210/611 |
| 4,704,259 | 11/1987 | Lipsztajn | 423/55 |
| 4,789,478 | 12/1988 | Revis et al. | 210/611 |
| 5,062,956 | 11/1991 | Lupton et al. | 210/611 |
| 5,155,042 | 10/1992 | Lupton et al. | 435/262.5 |
| 5,221,159 | 6/1993 | Billings et al. | 405/128 |
| 5,227,518 | 7/1993 | Cavazza | 560/253 |

OTHER PUBLICATIONS

"Chromium Remediated by Biological Treatment", Egnineering and Mining Journal, Aug. 1994 (Maclean Hunger Publishing Company (1994).

Witmer, Charlotte, "*Panel Discussion: Exposure, Remediation, and Related Research Needs*", Environmental Health Perspectives, vol. 92, pp. 139–140 (1991).

*Primary Examiner*—Carolyn Paden
*Attorney, Agent, or Firm*—Thorpe North & Western

[57] ABSTRACT

A method of reducing the concentration of Cr(VI) in a liquid aqueous residue comprises the steps of providing anaerobic Cr(VI) reducing bacteria, mixing the liquid aqueous residue with a nutrient medium to form a mixture, and contacting the mixture with the anaerobic Cr(VI) reducing bacteria such that Cr(VI) is reduced to Cr(III). The anaerobic Cr(VI) reducing bacteria appear to be ubiquitous in soil and can be selected by collecting a soil sample, diluting the soil sample with a sterile diluent to form a diluted sample, mixing the diluted sample with an effective amount of a nutrient medium and an effective amount of Cr(VI) to form a mixture, and incubating the mixture in the substantial absence of oxygen such that growth of Cr(VI) sensitive microorganisms is inhibited and growth of the anaerobic Cr(VI) reducing bacteria is stimulated. A method of in situ bioremediation of Cr(VI) contaminated soil and/or groundwater is also disclosed.

35 Claims, 10 Drawing Sheets

METHOD FOR IN SITU OR EX SITU BIOREMEDIATION OF HEXAVALENT CHROMIUM CONTAMINATED SOILS AND/OR GROUNDWATER

CONTRACTUAL ORIGIN OF THE INVENTION

The United States Government has rights in this invention disclosed under Contract Number DE-AC07-76ID01570 between the U.S. Department of Energy and EG&G Idaho, Inc., now Contract Number DE-AC07-94ID13223 with Lockheed Idaho Technologies Company.

BACKGROUND OF THE INVENTION

This invention relates to methods of remediating environmental pollution. More particularly, the invention relates to methods for in situ and ex situ bioremediation of soils and/or groundwater contaminated with hexavalent chromium (Cr(VI)).

Cr(VI) compounds, primarily in the forms of chromate ($CrO_4^{2-}$) and dichromate ($Cr_2O_7^{2-}$), are common environment pollutants in soils and water. These compounds have become widely distributed in the environment from their use in a variety of commercial processes, such as rust proofing, metal plating, and manufacture of dyes and inks, as well as chromite ore processing. As a result of contaminated discharges from these industrial applications and inappropriate waste disposal practices, significant amounts of chromate and dichromate have contaminated the environment. T. Burke et al., Chromite Ore Processing Residue in Hudson, County, N.J., 92 Environmental Health Perspectives 131–37 (1991); R. G. Riley & J. M. Zachara, Nature of Chemical Contaminants on DOE Lands and Identification of Representative Contaminant Mixtures for Basic Subsurface Science Research, OHER Subsurface Science Program (PNL, Richland, Wash., 1991).

As an environmental pollutant, Cr(VI) represents a considerable health risk. C. Witmer, Panel Discussion: Exposure, Remediation, and Related Research Needs, 92 Environmental Health Perspectives 139–40 (1991). The toxicity of Cr(VI) has been well established in man as well as animals and plants. J. H. Rediske, Chromium Toxicity in Plants, Annual Report for 1955/56, HW 41500:48 (Hanford Biological Research, Richland, Wash., 1956); G. Mance, Pollution Threat of Heavy Metals in Aquatic Environments 31–60, 134–35 (1987); P. A. Olson & R. F. Foster, Effect of Chronic Exposure to Sodium Dichromate on Young Chinook Salmon and Rainbow Trout, Annual Report for 1955/56, HW 41500:35 (Hanford Biological Research, Richland, Wash., 1956). Human exposure to Cr(VI) can result in ulceration of skin, eyes, and mucous membranes, as well as mutagenic and carcinogenic effects. C. Witmer, Panel Discussion: Exposure, Remediation, and Related Research Needs, 92 Environmental Health Perspectives 139–40 (1991). It has been projected that Cr(VI) pollution will be an environmental problem 1000 years from now unless contamination is remedied. L. Xing & D. Okrent, Future Risk from a Hypothesized RCRA Site Disposing of Carcinogenic Metals Should a Loss of Societal Memory Occur, 38 J. Hazardous Materials 363–84 (1993).

Methods of remediation of hexavalent chromium contamination include isolation of a site (e.g., covering with asphalt), "remove and treat" processes, and in situ treatment. Each of these categories of treatment has certain risks, but risks can be minimized with techniques that do not involve movement of hazardous material, i.e. in situ treatment.

Upon reduction of Cr(VI) to trivalent chromium (Cr(III)), the toxic effects are significantly reduced in humans, animals, and plants due to decreased solubility and bioavailability of Cr(III). C. Cervantes, Bacterial Interactions with Chromate, 59 Antonie van Leeuwenhoek 229–33 (1991). There are basically two types of chemical reduction processes in use today, one involving ferrous iron and the other sodium bisulfate. The bisulfate method requires several pH changes, from alkaline to acid and back to alkaline, to permit all of the necessary chemical reactions to take place. In the method using ferrous iron, large amounts of sludge are formed.

Recently, microorganisms capable of directly reducing Cr(VI) to Cr(III) have been discovered. This phenomenon was first reported in the 1970's, when it was determined that certain strains of Pseudomonas isolated from chromate-containing sewage sludges were capable of reducing chromate, dichromate, and crocoite ($PbCr_4$) during anaerobic growth. E. V. Lebedeva & N. N. Lyalikova, Reduction of Crocoite by *Pseudomonas chromatophila* Species Nova, 48 Mikrobiologiya 517–22 (1979); V. I. Romanenko & V. N. Korenkov, A Pure Culture of Bacteria Utilizing Chromates and Bichromates as Hydrogen Acceptors in Growth under Anaerobic Conditions, 46 Mikrobiologiya 414–17 (1977). Since these initial reports, several additional chromate-reducing bacteria have been reported, including other strains of Pseudomonas as well as species of Achromobacter, Aeromonas, Bacillus, Enterobacter, Escherichia, and Nicrococcus. L. H. Bopp & H. L. Ehrlich, Chromate Resistance and Reduction in *Pseudomonas fluorescens* strain LB300, 150 Arch. Microbiol. 426–31 (1988); P. I. Gvozdyak et al., Reduction of Hexavalent Chromium by Collection Strains of Bacteria, 55 Mikrobiologiya 962–65 (1986); H. Horitsu et al., Enzymatic Reduction of Hexavalent Chromium by Hexavalent Chromium Tolerant *Pseudomonas ambigua* G-1, 51 Agric. Biol. Chem. 2417–20 (1987); E. I. Kvasnikov et al., New Gram-Variable Bacterium Which Reduces Chromium and Has a Mixed Type of Flagellation, 54 Mikrobiologiya 83–88 (1985); E. I. Kvasnikov et al., Bacteria Reducing Chromium in Nature and in Industrial Sewage, 57 Mikrobiologiya 680–85 (1988); P. Wang et al., Isolation and Characterization of an *Enterobacter cloacae* Strain that Reduces Hexavalent Chromium under Anaerobic Conditions, 55 Appl. Environ. Microbiol. 1665–69 (1989).

Recent reports have demonstrated the feasibility of using bioprocesses for the treatment of Cr(VI)-containing wastes incorporating pure cultures of Cr(VI)-reducing bacteria. W. A. Apel & C. E. Turick, Bioremediation of Hexavalent Chromium by Bacterial Reduction, in Mineral Bioprocessing (R. W. Smith & M. Mishra eds., 1991); P. C. DeLeo & H. L. Ehrlich, Reduction of Hexavalent Chromium by *Pseudomonas fluorescens* LB300 in Batch and Continuous Cultures, 40 Appl. Microbiol. Biotech. 756–59 (1994); L. Fude et al., Reduction of Cr(VI) by a Consortium of Sulfate-Reducing Bacteria (SRBIII), 60 Appl. Environ. Microbiol. 1525–31 (1994); K. Fujie et al., Development of Bioreactor System for the Treatment of Chromate Wastewater using *Enterobacter cloacae* HO-1, 30 Water Sci. Technol. 235–43 (1994); R. Gopolan & H. Veeramani, Studies on Microbial Chromate Reduction by Pseudomonas sp. in Aerobic Continuous Suspended Growth Cultures, 43 Biotechnol. Bioeng'g 471–76 (1994). Moreover, bioremediation offers the advantages of low cost, simplicity, safety, and versatility. However, the use of pure cultures of bacteria to treat Cr(VI) contaminated soil wash effluents or groundwater presents several problems. For example, sterilization of a nonsterile soil effluent entering a bioreactor containing a pure culture would be prohibitively expensive. Moreover, a nonsterile input into a bioreactor can introduce Cr(VI)-resistant, non- (Cr(VI)-reducing microorganisms that can eventually outcompete the pure culture, rendering the bioprocess inefficient. It would be advantageous, therefore, to develop a bioprocess utilizing selected indigenous microbes that are both Cr(VI)-resistant and Cr(VI)-reducing. Under aerobic conditions, a Cr(VI)-resistant microbial consortium with minimal Cr(VI) reducing capability would predominate because Cr(VI) reducing bacteria would have a growth disadvantage from having to expend energy to reduce Cr(VI). Efficient bacterial reduction of Cr(VI) is thus more likely to occur anaerobically, primarily due to the ability of many facultative anaerobes to use Cr(VI) as a terminal electron acceptor. E.g., P. C. Wang et al., Membrane-Bound Respiratory System of *Enterobacter cloacae* strain HP1 Grown Anaerobically with Chromate, 78 FEMS Microbiol. Lett. 11–16 (1991).

Billings et al., U.S. Pat. No. 5,221,159, describes methods and processes for in situ removal of contaminants, such as organic and inorganic products, from soil and groundwater by providing one or more injection wells drilled to a depth below the water table and an extraction well drilled to a depth above the water table. Oxygenated gas is injected under pressure through the injection well while vacuum is applied to the extraction well. Contaminants are removed from the groundwater and vadose zone by a combination of physical, chemical, and biochemical processes. Microbes from the contaminated site are extracted and analyzed to determine the genera present in the samples. Microbes from genera known to be useful in biodegrading the contaminants are then isolated, and the isolated microbes are fermented to increase the numbers of useful organisms. Then the fermented microorganisms are reintroduced through the injection or extraction wells to enhance biodegradation. If necessary, because of low levels of contaminants and consequent low levels of microbes, a food source is provided to the microbial population to sustain high levels of degradation activity. This method suffers from requiring the labor-intensive and time-consuming work of identifying genera in the microbial population at the contaminated site and isolating microbes from genera that are known to biodegrade the contaminants.

M. Lipsztajn, U.S. Pat. No. 4,704,259, discloses a method of removing soluble hexavalent chromium from aqueous chlorate solutions by adding hydroxide ions and dithionite ions such that each is present in a mole ratio of at least 3:1 with respect to dichromate ions. Hexavalent chromium is reduced to trivalent chromium, with the trivalent chromium precipitating as chromic hydroxide ($Cr(OH)_3$). This process is designed for removing sodium dichromate from cell liquor produced by electrolysis of sodium chloride, and is not seen to by useful for in situ remediation of environmental contamination.

J. W. Kauffman et al., U.S. Pat. No. 4,522,723, teaches a process for reducing the concentration of water soluble ionic heavy metal species and sulfate ions in aqueous waste solutions. The principal focus of this patent appears to be reducing uranium and molybdenum in mining waste waters, but it is suggested that the method can be used with metals from many groups of the Periodic Table including Group VIb, which includes chromium. There is no indication, however, that the method has been applied to chromium-containing soil and/or groundwater. In this method the waste solution is passed through a porous matrix on which a bacterial population of Desulfovibrio and/or Desulfotomaculum resides. Under anaerobic conditions the water soluble sulfate ions are converted to hydrogen sulfide, and the soluble heavy metals react with the hydrogen sulfide to produce insoluble heavy metal species that are retained on and recoverable from the porous matrix. This process requires adding sulfate ions to the contaminated solution and is not suitable for in situ treatment of chromium contamination of the environment.

L. H. Bopp, U.S. Pat. No. 4,468,461, discloses a method of reducing hexavalent chromium in waste water to trivalent chromium by passing the contaminated waste water through a series of holding ponds inoculated with *Pseudomonas fluorescens* LB300. Under aerobic or anaerobic conditions the bacterium reduces the chromate. This method requires use of a purified culture of bacteria, which becomes contaminated with other organisms in the holding ponds. The method is not suitable for in situ remediation.

V. I. Romanenko et al., U.S. Pat. No. 3,941,691, describes a method of removing chromates and dichromates from industrial effluents wherein the industrial effluents are delivered to a sealed reactor, clarified domestic sewage and cultures of *Bacterium dechromaticans* are continuously fed into the reactor to form a mixture, the mixture is stirred continuously in the absence of oxygen such that the bacteria reduce the chromates and dichromates, and the mixture is continuously fed to a settling tank where the bacteria and reduced chromium compounds settle to leave chromate-depleted effluent. This process also requires use of purified bacterial cultures and is unsuitable for in situ remediation of soil and groundwater.

F. S. Lupton et al., U.S. Pat. No. 5,155,042, teaches a method of reducing Cr(VI) to insoluble Cr(III) in solid waste residues by contacting the solids with an acid to produce an aqueous solution having a pH of about 6.5 to 9.5, then adding sulfate-reducing anaerobic bacteria and a source of sulfates and nutrients for the bacteria. When the solid residues are below ground level, a continuous recirculation can be set up to extract Cr(VI) from the solid residues, treat the resulting Cr(VI)-containing solution above ground, and return the treated solution to the soil. This process involves both continued addition of acid to the soil to maintain the pH in the necessary range and use of pure cultures of bacteria. Further, it is not amenable to in situ remediation of chromium contamination.

F. S. Lupton et al., U.S. Pat. No. 5,062,956, discloses a method similar to that of U.S. Pat. No. 5,155,042, discussed above, except for relating to treatment of chromium-containing aqueous wastes. The pH of the aqueous residue is adjusted to pH 6.5 to 9.5 by addition of a neutralizing agent. Then a carbon source, sulfate, and nutrients are added to support growth of sulfate-reducing anaerobic bacteria. The aqueous residue is then diluted such that the Cr(VI) concentration is no more than 200 ppm, and the diluted residue is contacted with sulfate-reducing anaerobes under anaerobic conditions. This process can be conducted in a continuous bioreactor, but is not suitable for in situ bioremediation of contaminated sites.

N. W. Revis, U.S. Pat. No. 4,789,478, describes a process for converting heavy metal ions to metal sulfides by microorganisms. This process involves contacting an aqueous waste solution with a mixed culture of *Citrobacter freundii* and a dissimulatory sulfate reducer (e.g., Desulfomonas) in the presence of nutrients, whereby sulfide ions are produced and combine with the heavy metals, and the heavy metal sulfides are then precipitated from the waste solution. No reference is made to reduction of Cr(VI), purified cultures of bacteria are needed, and the process is unsuitable for in situ applications.

R. E. Beeman, U.S. Pat. No. 5,277,815, teaches a method of in situ biodegradation of halogenated organic compounds in groundwater by stimulation of bacteria. This process comprises the steps of determining the initial concentration of halogenated contaminants in the groundwater, providing an electron donor as a stimulus for anaerobic degradation of the compounds by indigenous bacteria, establishing and maintaining a sulfate reducing environment by addition of inorganic sulfate, monitoring the groundwater for increased concentrations of di- and mono-halogenated organic compounds, upon detecting these di-halogenated compounds converting the groundwater environment from anaerobic dehalogenating conditions to anaerobic methanogenic conditions, allowing methanogenic bacteria to further degrade the halogenated compounds to unsubstituted compounds, converting the anaerobic conditions to aerobic conditions by supplying a source of oxygen to activate aerobic bacteria, and allowing aerobic degradation of halogenated compounds to organic degradation procuts and ultimately to carbon dioxide and water. This process deals only with halogenated organic compounds and fails to suggest how inorganic contaminants, i.e. Cr(VI)-containing compounds, can be remediated.

In view of the foregoing, it will be appreciated that providing a method of bioremediation of hexavalent chromium contamination, wherein such method can also be adapted for ex situ and/or in situ/ex situ bioremediation, is not dependent on use of pure cultures of bacteria, and is operated under substantially anaerobic conditions would be a significant advancement in the art.

OBJECTS AND SUMMARY OF THE INVENTION

It is an object of the present invention to provide a method of bioremediation of hexavalent chromium contaminated soil and/or groundwater by reducing Cr(VI) to Cr(III).

It is also an object of the invention to provide a method of bioremediation of hexavalent chromium contaminated soil and/or groundwater that can be practiced in situ, ex situ, or in situ/ex situ.

It is another object of the invention to provide a method of selecting chromate reducing bacteria that can be used for bioremediation of hexavalent chromium contaminated soil and/or groundwater.

It is still another object of the invention to provide a method of bioremediation of hexavalent chromium contamination that is not dependent on use of pure bacterial cultures.

A method of reducing levels of Cr(VI) in a liquid aqueous residue comprises providing anaerobic Cr(VI) reducing bacteria, mixing the liquid aqueous residue with an effective amount of a nutrient medium to form a mixture, and contacting the mixture in the substantial absence of oxygen with the anaerobic Cr(VI) reducing bacteria such that the bacteria reduce the Cr(VI) to Cr(III). The liquid aqueous residue is preferably a member selected from the group consisting of groundwater, industrial effluent, waste water, soil wash, and mixtures thereof. The nutrient medium can be any compatible carbon and energy source for supporting bacterial growth. The contacting step is preferably performed in a bioreactor operating in continuous mode, and the bioreactor can contain a solid support or can be a continuously stirred reactor.

The anaerobic Cr(VI) reducing bacteria are selected by collecting a soil sample, diluting the soil sample with a sterile aqueous diluent to form a diluted sample, mixing the diluted sample with an effective amount of nutrient medium and an effective amount of Cr(VI) to form a selective mixture, and incubating the selective mixture in the substantial absence of oxygen for a suffient time and at a temperature such that growth of the anaerobic Cr(VI) reducing bacteria is stimulated. The effective amount of Cr(VI) is generally about 0.1 to about 25,000mg/L, preferably about 10 to about 750 mg/L, and more preferably about 50 to about 400 mg/L. The incubating step is preferably at a temperature of about 4° C. to about 65° C. for a time up to about 48 hours.

A method of in situ bioremediation for reducing the concentration of Cr(VI) in contaminated soil and/or groundwater comprises providing an effective amount of a nutrient medium and maintaining the contaminated soil and/or groundwater in substantial absence of oxygen whereby growth of indigenous Cr(VI) reducing bacteria is stimulated such that the bacteria reduce Cr(VI) to Cr(III).

DETAILED DESCRIPTION OF THE INVENTION

Figure 1:
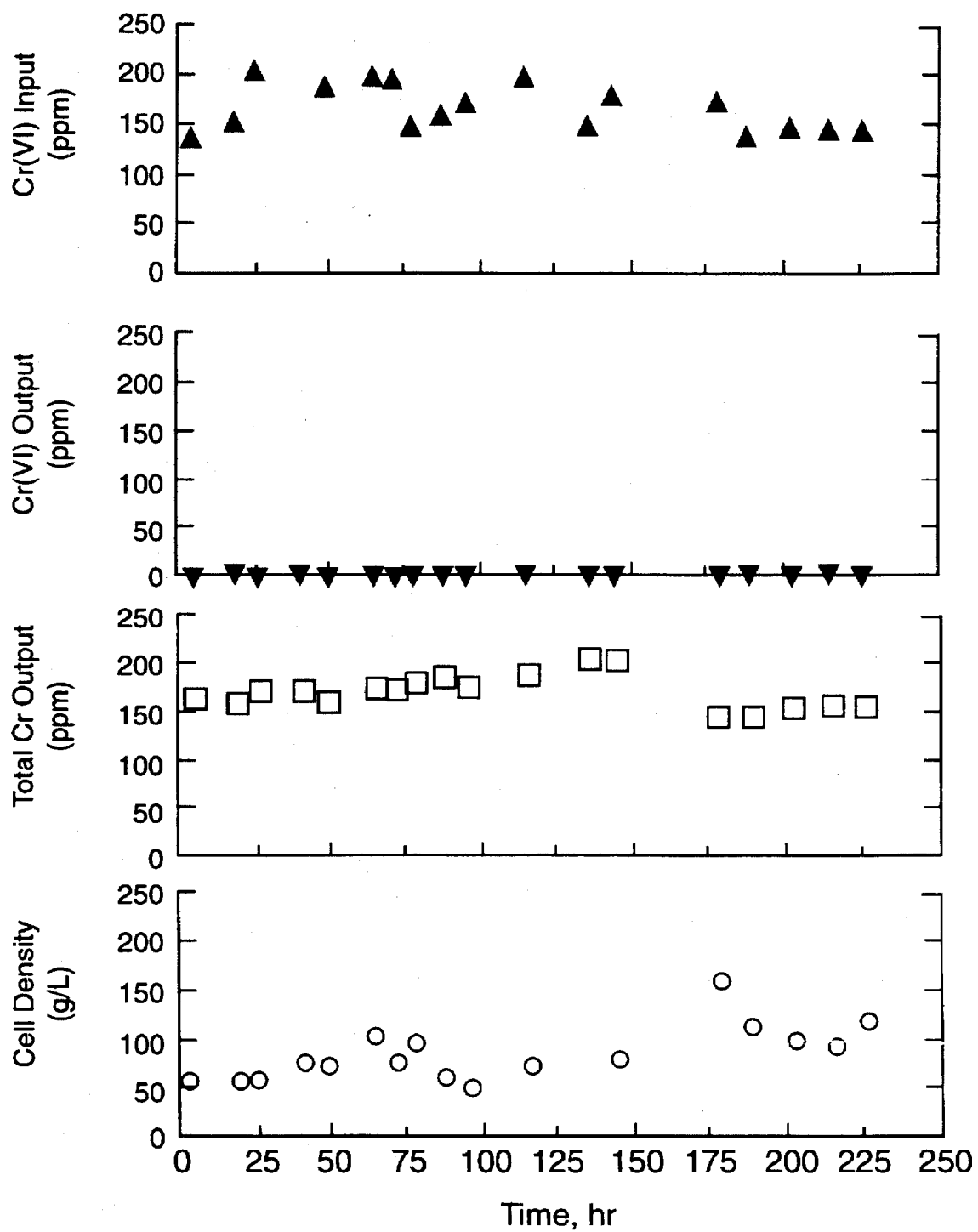
FIGS. 1–3 show results of operation of anaerobic bioreactors incorporating Cr(VI) facultative anaerobes from Cr(VI) contaminated soil: ▲—Cr(VI) input; ▼—Cr(VI) output; □—total Cr output; o—cell density; ●—pH.

Before the present methods for bioremediation of hexavalent chromium contaminated soil and/or ground water and selection of chromate reducing bacteria are disclosed and described, it is to be understood that this invention is not limited to the particular process steps and materials disclosed herein as such process steps and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "a bacterium"

includes reference to two or more bacteria, reference to "a carbon source" includes reference to a mixture of two or more of such carbon sources, and reference to "a liquid aqueous residue" includes reference to two or more of such liquid aqueous residues.

In describing and claiming the present invention, the following terminology will be used in accordance with the definitions set out below.

As used herein, "effective amount" means an amount of a liquid aqueous nutrient medium sufficient to maintain growth of anaerobic Cr(VI) reducing bacteria in the substantial absence of oxygen and at a temperature suffient to support growth of such bacteria. Such an an effective amount of liquid aqueous nutrient medium can be determined without undue experimentation by a person of ordinary skill in the art. An effective amount of Cr(VI) for use in selecting anaerobic Cr(VI) reducing bacteria from a soil sample means an amount sufficient to inhibit growth of Cr(VI) sensitive microorganisms without being substantially toxic to Cr(VI) reducing anaerobes. Generally, such an effective amount of Cr(VI) will be in the range of about 0.1 to about 25,000 mg/L, preferably 10 to about 750 mg/L, and more preferably in the range of about 50 to about 400 mg/L.

As used herein, "liquid aqueous residue" means a liquid aqueous solution and/or suspension that is contaminated with Cr(VI) and is to be treated by the instant process to reduce Cr(VI) to Cr(III), resulting in bioremediation of the Cr(VI) contamination. Such liquid aqueous residue can include contaminated groundwater, industrials effluent, waste water, soil wash, mixtures thereof, and concentrated or diluted solutions derived therefrom that can be pumped to a bioreactor for treatment according to methods known in the art. For example, soil can be excavated from a contaminated site, washed with a predesigned chemical treatment to extract Cr(VI) from the soil, and the Cr(VI) contaminated soil wash conducted to a bioreactor for treatment.

As used herein, "substantial absence of oxygen," "substantially anaerobic," or similar terms mean that the oxygen tension is sufficiently low such that facultative anaerobes are able to respire using Cr(VI) as as a terminal electron acceptor.

As used herein, "nutrient medium" means a liquid, aqueous solution containing a carbon source and energy source for supporting growth of bacteria, wherein such carbon and energy source is compatible with anaerobic, bacteria-mediated Cr(VI) reduction. It has been found that many conventional microbial carbon and energy sources function adequately as a nutrient medium with the exception of alcohols and sugar alcohols. Such conventional carbon and energy sources include carbohydrates, amino acids, organic acids, nitrogen sources (e.g., urea), and mixtures thereof. Amino acids are good carbon and energy sources, but are relatively expensive. Acetic acid and salts thereof are also good carbon and energy sources. Molasses, urea, casamino acid, organic wastes, and the like are preferred because of their relative low cost.

As summarized above, a method of reducing levels of Cr(VI) in a liquid aqueous residue comprises providing anaerobic Cr(VI) reducing bacteria selected from a soil sample, mixing the liquid aqueous residue with an effective amount of a nutrient medium to form a mixture, and contacting the mixture in the substantial absence of oxygen with the selected anaerobic Cr(VI) reducing bacteria for a sufficient time and at a temperature such that the bacteria reduce the Cr(VI) to Cr(III). Reduction of Cr(VI) to Cr(III) renders the chromium insoluble and unavailable for uptake by organisms, thus effecting remediation of the contamination.

The Cr(VI) reducing bacteria used for bioremediation of Cr(VI) contamination are selected from soil. It is believed that such Cr(VI) reducing bacteria are ubiquitous in soil and sediments, as shown by experiments described in detail below. A soil sample is collected, and the soil sample is diluted with a sterile aqueous diluent to extract the bacteria from the soil matrix and suspend the bacteria. The diluent can be any aqueous medium that is compatible with maintaining viability of the bacteria, such as a physiological saline solution or phosphate buffer. The diluted bacteria are then mixed with an effective amount of nutrient medium and an effective amount of Cr(VI) to form a selective mixture, and the selective mixture is incubated in the substantial absence of oxygen for a time and at a temperature whereby Cr(VI)-reducing bacteria in the mixed bacterial population are stimulated to grow such that they predominate. Under these conditions, i.e. a substantially anaerobic environment containing Cr(VI), Cr(VI)-reducing bacteria in the mixed bacterial population use Cr(VI) as a terminal electron acceptor and, thus are able to grow and reduce Cr(VI). Aerobic bacteria in the mixed bacterial population will not grow because of the lack of oxygen and inability to use Cr(VI) as a terminal electron acceptor. Cr(VI)-sensitive anaerobes will be killed or will not grow due to the presence of Cr(VI). Cr(VI)-resistant, non-Cr(VI)-utilizing anaerobes are able to grow and reduce Cr(VI), but do so merely as a detoxification mechanism and by expending energy. Thus, such non-Cr(VI)-utilizing bacteria are at a competitive disadvantage and will be out-competed by the Cr(VI)-reducing bacteria. The effective amount of Cr(VI) for selecting the Cr(VI)-reducing bacteria will generally be in the range of about 0.1 to about 25,000 mg/L, preferably in the range of about 10 to about 750 mg/L, and more preferably in the range of about 60 to about 400 mg/L. The nutrient medium can be the same or different than the nutrient medium used during bioremediation of Cr(VI) contamination. Temperatures in the range of about 4° C. to about 65° C. are generally preferred, but the temperature can vary according to process and economic considerations. A person of ordinary skill in the art can select such temperature conditions without undue experimentation. Under these conditions, anaerobic Cr(VI)-reducing bacteria predominate in the bacterial population within about 24 to 48 hours.

The selection of the anaerobic Cr(VI)-reducing bacteria and the step of contacting the mixture of liquid aqueous residue and nutrient medium are preferably carried out in a bioreactor. The selection of bacteria could also be done in a separate bioreactor from the one in which the contacting step takes place. The bioreactor can be of any suitable design, such as a packed bed reactor containing a solid support or a continuously stirred reactor. Activated carbon and ceramic solid support have been used with good results. It is preferred to operate the bioreactor in continuous mode rather than batch mode as will be shown in the examples below.

The invention can also be practiced by in situ remediation of Cr(VI) contamination in groundwater and/or soil. This process can be conceptualized as one in which a portion of the earth acts as a bioreactor. A method of in situ remediation of Cr(VI) contamination comprises stimulating growth of indigenous anaerobic Cr(VI) reducing bacteria in the contaminated soil and/or groundwater by adding a nutrient medium to the soil and/or groundwater and maintaining a substantially anaerobic environment. By providing a nutrient medium and maintaining a substantially anaerobic environment, together with the Cr(VI) in the groundwater and/or soil, an environment is created whereby indigenous Cr(VI)-reducing bacteria in the soil are stimulated to grow and predominate in the soil, similar to what occurs in a bioreactor. These bacteria reduce the contaminating Cr(VI) to Cr(III), thus remediating the contamination.

EXPERIMENTAL

Example 1

Soil samples were collected in sterile containers from a chromate contaminated site and stored at 4° C. Soil extracts ($10^{-3}$ g/ml) were made with isotonic phosphate buffer and were used to inoculate sealed serum vials containing Tryptic Soy Broth (TSB, Difco, Detroit, Mich.) with $N_2$ in the headspace. Cr(VI) was added to the culture broth as $K_2CrO_4$ to a final concentration of about 20 mg/l of Cr(VI). These vials were then incubated at 30° C. on a gyratory shaker at 100 rpm.

The resulting mixed culture was used to inoculate TSB containing 10–60 mg/L of Cr(VI) in a 1.4 liter chemostat at 30° C. with a dilution rate of 0.5/day. After 250 hours of operation of the chemostat, cells were harvested and added to a packed bed reactor with sterile ceramic saddles as a solid support. The liquid volume of the packed bed reactor was 1 liter. Growth conditions were similar to those in the chemostat. The reactor was operated in batch mode for 48 hours with an initial Cr(VI) concentration of 200 mg/L, and then operated continuously with Cr(VI) concentrations maintained at 140–200 mg/L with a syringe pump that continuously added Cr(VI) to the medium upstream of an in line mixer. Nutrients and Cr(VI) were circulated through the reactor with a peristaltic pump positioned downstream of the reactor.

Samples were taken periodically of the Cr(VI) concentrations entering the reactor, and Cr(VI), total Cr, pH, and bacterial cell density in the effluent were also determined. At the end of the experiment, the preweighed ceramic saddles were dried at 103° C. to determine the dry weight of the bacterial cells.

FIG. 1 shows that complete reduction of the Cr(VI) to Cr(III) was achieved by the selected microbial consortium. The increase in bacterial cell density is attributable to growth of the Cr(VI)-reducing bacteria in the population. Thus, chromate contaminated soil contains anaerobic, Cr(VI)-reducing bacteria that can be selected rapidly in an anaerobic growth environment comprising a rich growth medium and high concentrations of hexavalent chromium.

Example 2

Figure 2:
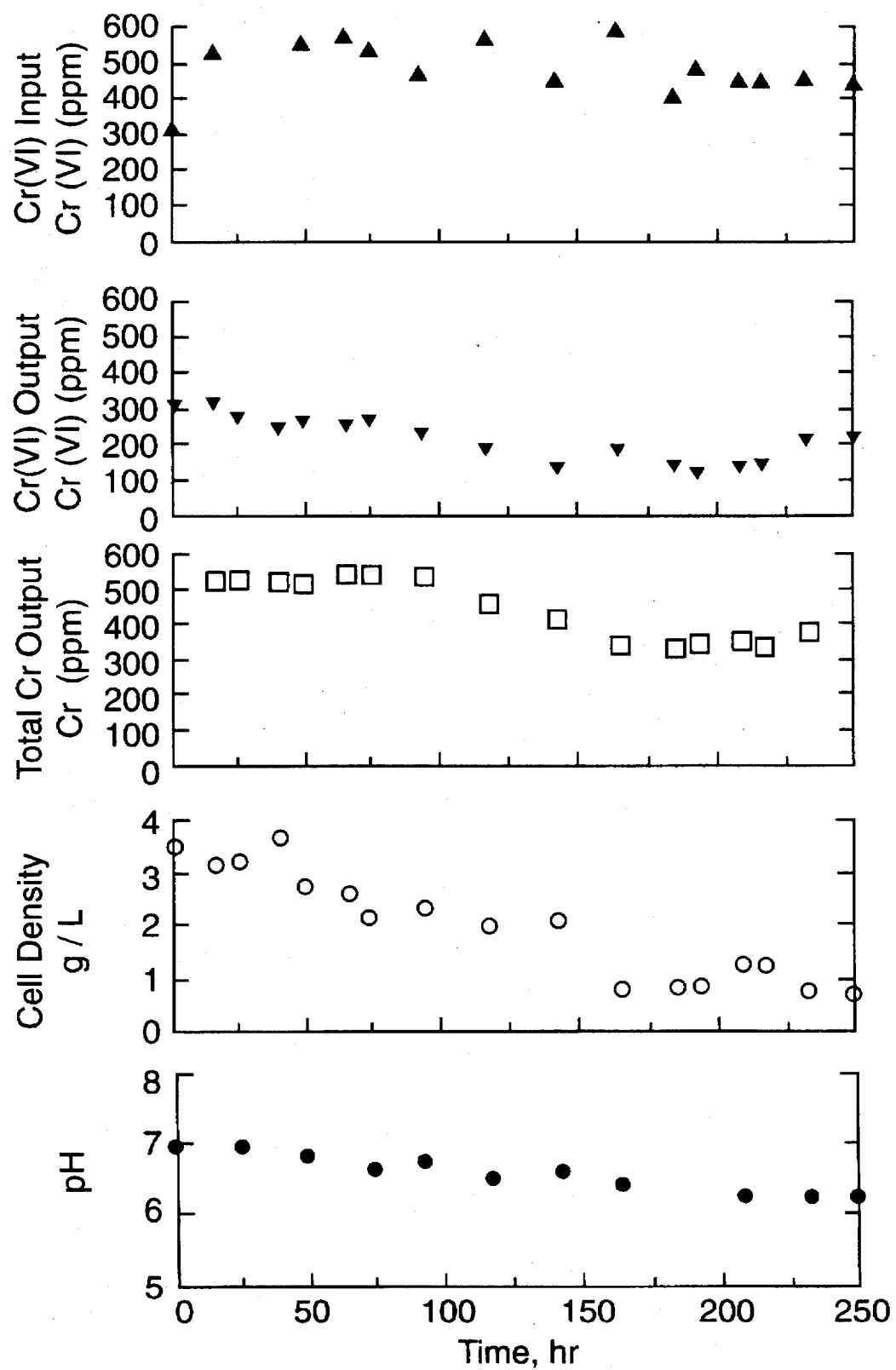

The procedure of Example 1 was followed with the exception that input Cr(VI) concentrations were increased to 300–600 mg/L to determine the maximum rate of reduction and that the ceramic saddles were not sampled at the conclusion of the experiment to determine bacterial dry weight. FIG. 2 shows the microbial consortium in the reactor significantly decreased the concentration of Cr(VI) in the ouput, but that complete reduction of Cr(VI) to Cr(III) was not achieved so that the maximum reduction rate could be calculated. Total chromium concentrations in the effluent were consistent with the Cr(VI) concentrations in the input for the first 100 hours, after which total chromium concentrations in the effluent decreased by about 20 percent. This decrease paralleled a decrease in bacterial density in the effluent, suggesting that chromium adsorption to nonviable cells may have decreased total chromium concentrations in the effluent. This decrease was a result of operating the reactor in batch mode prior to beginning continuous operation.

Example 3

Figure 3:
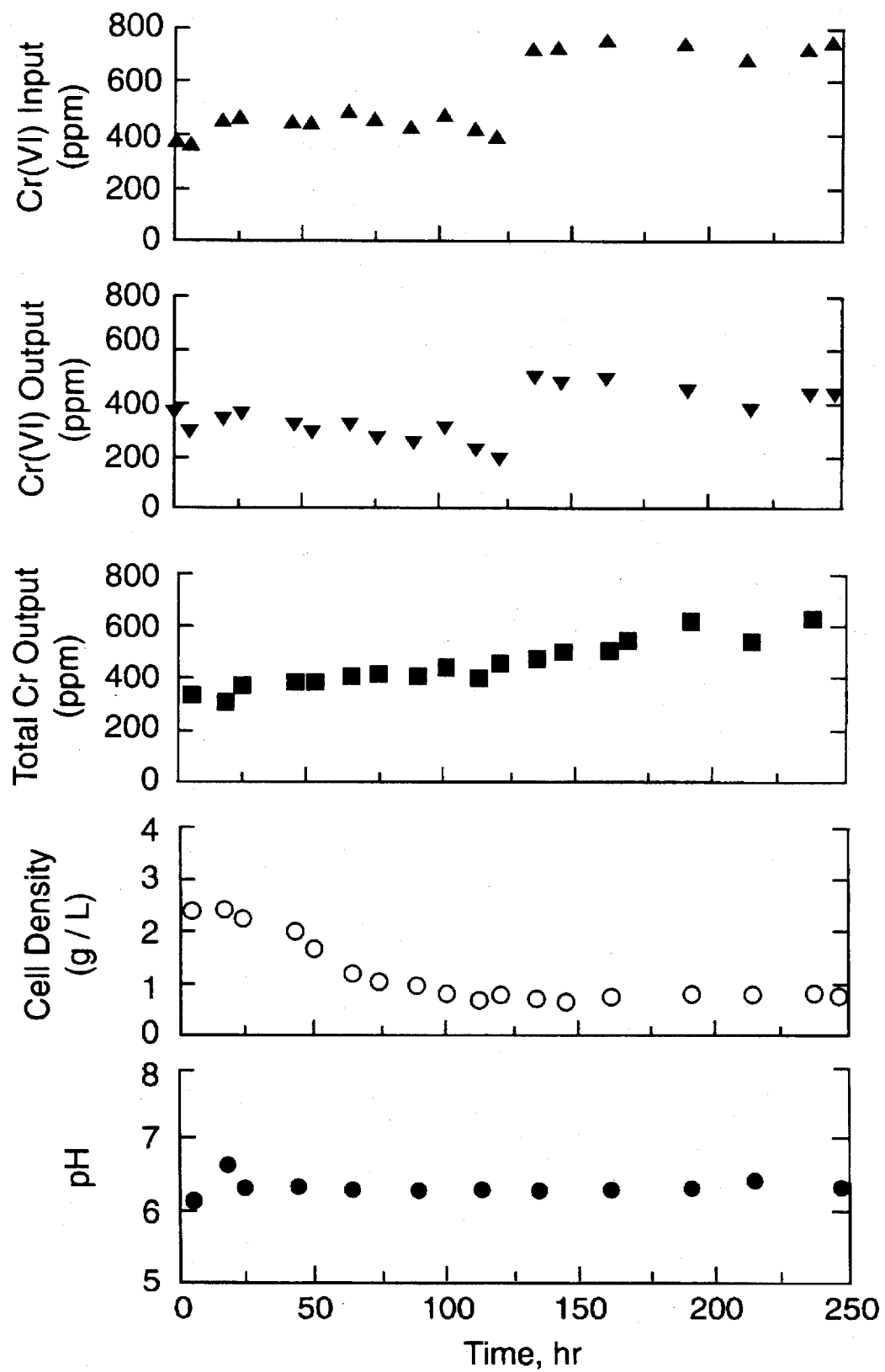

The procedure of Example 1 was followed with the exception that the reactor was operated in batch mode at a concentration of 400 mg/L of Cr(VI), and was operated in continuous mode at Cr(VI) concentrations of 350–750 mg/L. FIG. 3 shows the bacterial consortium in the reactor significantly reduced the concentration of Cr(VI) in the ouput, but that complete reduction of Cr(VI) to Cr(III) was not achieved so that the maximum rate of reduction could be calculated. Nevertheless, Cr(VI) reduction to Cr(III) occurred at input concentrations as high as 750 mg/L Cr(VI). As in Example 2, total chromium concentrations in the effluent were consistent with the Cr(VI) concentrations in the input for the first 100 hours, after which total chromium concentrations in the effluent decreased by about 20 percent. This decrease also paralleled a decrease in bacterial density in the effluent, suggesting that chromium adsorption to nonviable cells may have decreased total chromium concentrations in the effluent.

Example 4

Figure 4:
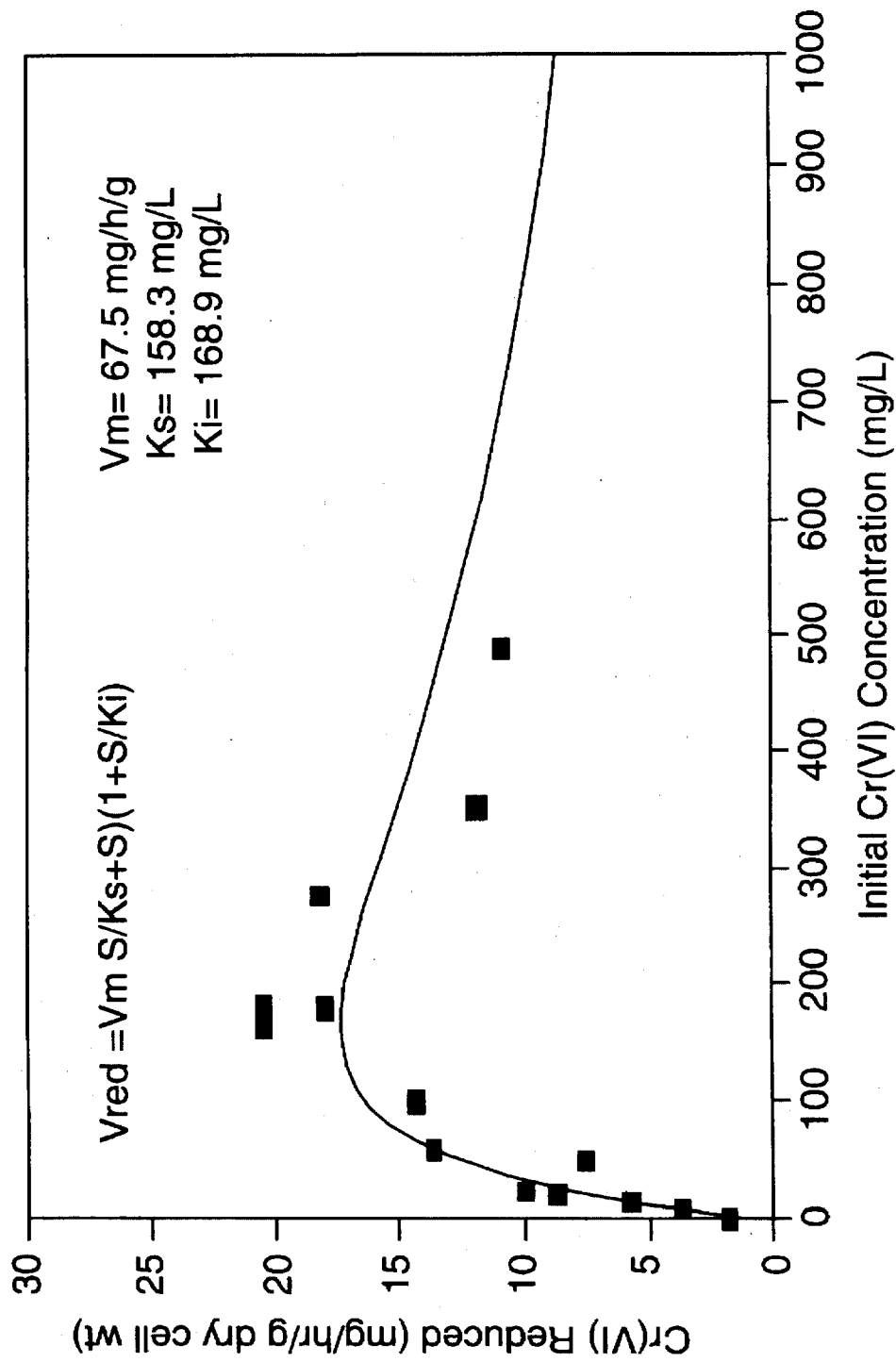
FIG. 4 shows determination of Cr(VI) reduction rate as a function of Cr(VI) concentration, wherein the data points (■) represent batch studies.

FIG. 4 shows the rate of Cr(VI) reduction as a function of Cr(VI) concentration as determined from batch studies conducted in Examples 1–3. The equation $V_{red}=V_m \cdot S/(K_s+S)(1+S/K_i)$, where $V_{red}$ is the specific rate of Cr(VI) reduction, was used to determine the maximum Cr(VI)reduction rate ($V_m$), Cr(VI) concentration (S), half saturation constant ($K_s$), and Cr(VI) inhibition constant ($K_i$). These parameters are expressed in the Table 1.

TABLE 1

| Parameter | Value |
|---|---|
| $V_m$ | 67.5 mg/h/g |
| $K_s$ | 158.3 mg/l |
| $K_i$ | 168.9 mg/l |

The maximum rate of reduction of Cr(VI) to Cr(III) observed was 6.9 mg/L/h (0.71 mg/g/h). Cr(VI) reduction occurred at input concentrations as high as 750 mg/L of Cr(VI) (FIG. 3), which is corroborated by values obtained in the batch kinetic study (FIG. 4). These results give a general idea of the kinetics that can be achieved with the present invention. It is anticipated that better results could be achieved, for example with bacteria from other environments.

Example 5

Figure 5:
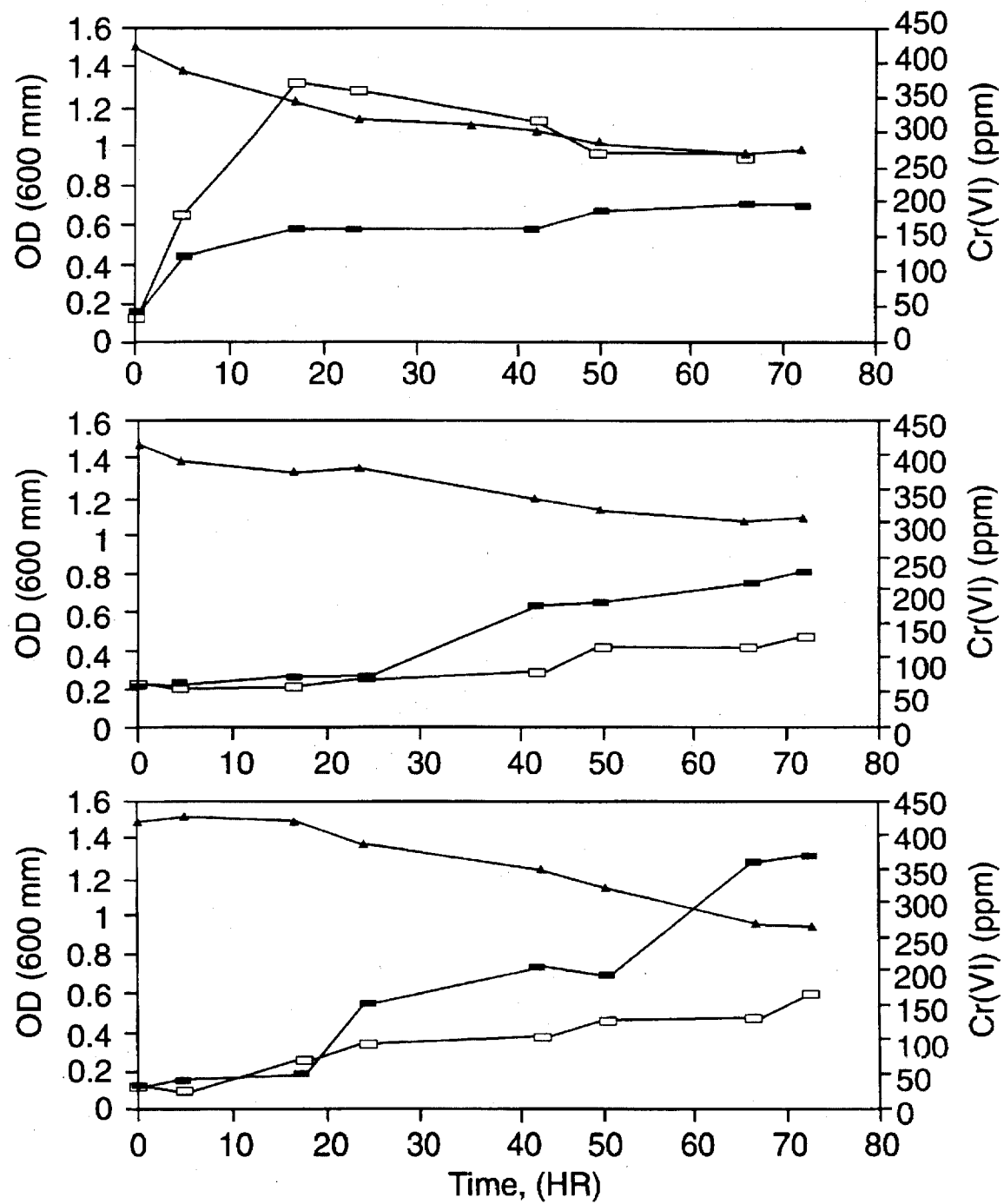
FIG. 5 shows anaerobic growth and Cr(VI) reduction of predominant bacterial strains isolated from an anaerobic Cr(VI) reducing bioreactor: ■—growth in the presence of Cr(VI); □—growth in the absence of Cr(VI); ▲—Cr(VI) concentrations.

The dominant bacterial strains that emerged in Examples 1–3 were evaluated. Three different strains, LWS1, SYS1, and SWS1 predominated. Strain LWS1 predominated during the early stages of continuous operation, but the population shifted after 100 hours of operation such that strains SYS1 and SWS1 emerged as the dominant strains in the population. Strain LWS1 demonstrated better growth when incubated anaerobically without Cr(VI), whereas strains SYS1 and SWS1 grew better when incubated anaerobically with Cr(VI) (FIG. 5). Because strains SYS1 and SWS1 eventually dominated the population of the reactor, the success of the strategy to provide an environment that selects Cr(VI)-reducing anaerobes is demonstrated.

Example 6

Soil samples were collected from a Cr(VI) contaminated site and from several uncontaminated areas. Samples were obtained from the following locations: CAS—arid soil from processed chromite ore slag containing about 25 ppm Cr(VI); RCSM—soil from a reclaimed coal strip mine in southwestern Pennsylvania; AG—agricultural soil from southeastern Idaho; GSS—geothermal spring sediment from the Salmon National Forest in north-central Idaho; NCF—northern coniferous forest soil from the Salmon National Forest in north-central Idaho; VHF—virgin hemlock forest soil from northern West Virginia; EDF—eastern deciduous forest soil from northern West Virginia; and NCSS—northern coniferous forest stream sediment from the Sawtooth Mountains in central Idaho.

Immediately after collection in sterile containers, the soil samples were stored at 4° C. for 30 days before use. Soil dilutions ($10^{-1}$ g/mL) were made in sterile isotonic phosphate buffer. One mL of each soil dilution was inoculated into 165 mL sealed serum vials containing 50 mL of TSB with $N_2$ in the headspace. The serum vials and their contents were sterilized prior to inoculation.

Control soils were prepared by autoclaving soil samples for 30 minutes per day for 4 consecutive days. Sterile soil dilutions were prepared as described above.

Cr(VI) was added to the culture broth as $K_2CrO_4$ to a final concentration of about 20 mg/L of Cr(VI). Cultures were incubated, at 30° C. on a gyratory shaker at 100 rpm, in an inverted position to limit gas leakage. Samples were analyzed periodically for Cr(VI) concentration and cell density.

Cr(VI) concentrations were measured by clarifying the solutions to be measured by centrifugation at 10,000 g for 5 minutes, diluting the clarified solution 1:5 or 1:10, adding 0.09 g of ChromaVer 3 Chromium Reagent Powder, and measuring absorbance at 542 nm.

Figure 6:
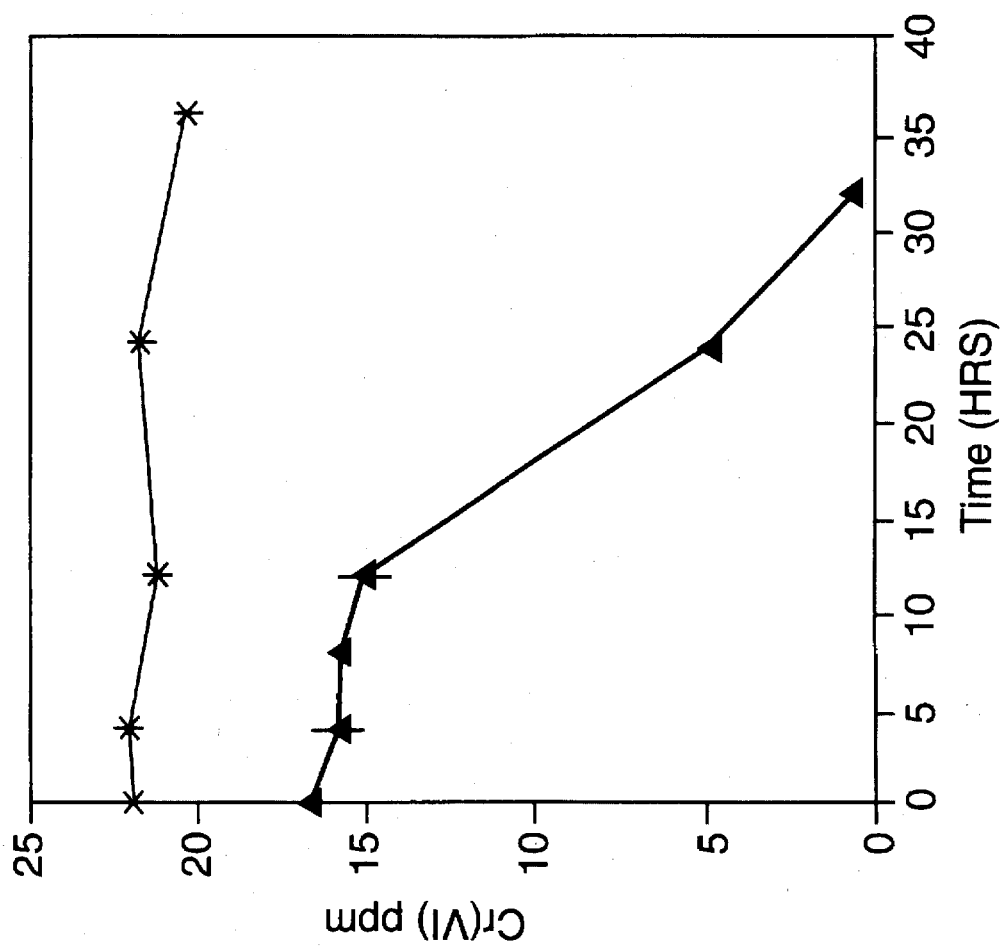
FIG. 6 shows anaerobic Cr(VI) reduction in the presence of nonsterile (▲) and sterile (*) soils from several chromate-contaminated and non-chromate-contaminated sites: CAS, RCSM, AG, GSS, and NCSS.
Figure 7:
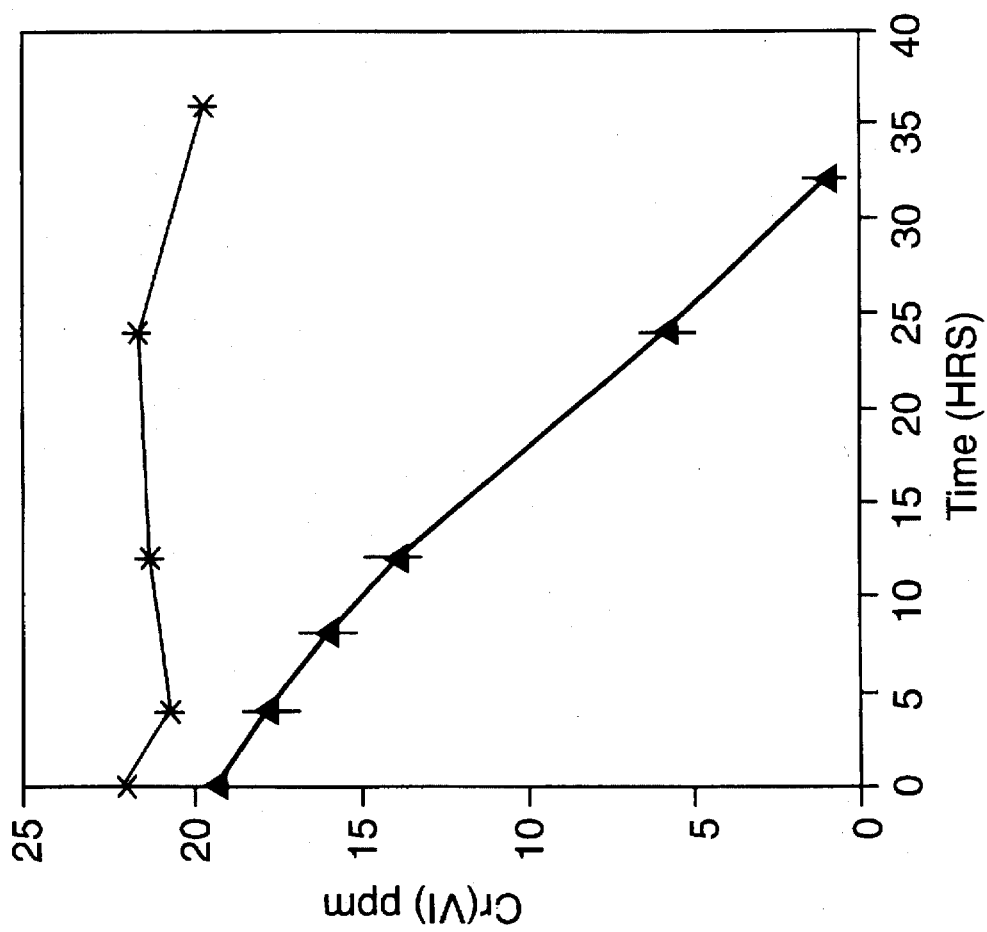
FIG. 7 shows anaerobic Cr(VI) reduction in the presence of nonsterile (▲) and sterile (*) soils from several non-chromate-contaminated sites: NCF, VHF, and EDF.

FIGS. 6 and 7 show that unsterilized soil samples from Cr(VI) contaminated soil and from uncontaminated soil reduce Cr(VI) to a much greater degree than sterilized, control soil samples within 32 hours. FIG. 6 represents the results with CAS, RCSM, AG, GSS, and NCSS, and FIG. 7 represents results with NCF, VHF, and EFG. Minimal Cr(VI) reduction occurred with the sterilized controls, therefore minerals present in the soils had little effect on Cr(VI) reduction. Hence, Cr(VI) reducing anaerobes occur in numerous and diverse environments, both contaminated and uncontaminated with Cr(VI). This indicates that Cr(VI)-reducing anaerobic bacteria may be ubiquitous in soils and sediments.

Example 7

After 32 hours of growth, pH, Eh, and total chromium levels of the cultures of Example 6 were determined. The initial pH of TSB was 7.04. Eh was measured with a platinum electrode (Microelectrodes, Inc., Londonderry, N.H.) using an ACCUMET 50 digital pH meter (Fisher Scientific, Pittsburgh, Pa.). Total chromium was analyzed with inductively coupled plasma emission spectroscopy (Model 3410, ARL) of clarified cultures. The results of these determinations are shown in Table 1.

TABLE 1

| Soil | pH | Eh (mV) | Total Cr (%) |
| --- | --- | --- | --- |
| CAS | 6.10 | −141 | 88 |
| RCSM | 6.20 | −133 | 101 |
| AG | 6.17 | −126 | 95 |
| GSS | 6.13 | −114 | 98 |
| NCF | 6.09 | −143 | 91 |

TABLE 1-continued

| Soil | pH | Eh (mV) | Total Cr (%) |
| --- | --- | --- | --- |
| VHF | 6.06 | −124 | 81 |
| EDF | 6.10 | −128 | 80 |
| NCSS | 7.57 | −244 | 95 |

These results show that total chromium concentrations in the cell-free supernatants were consistent with initial concentrations of Cr(VI). There was no evidence of Cr(III) precipitating out of solution or bacterial growth inhibition related to Cr(III). The pH changed little from the initial pH values of about 7.0.

Example 8

After Cr(VI) reduction occurred in the serum vials containing soil dilutions in Example 6, 1 mL of liquid was transferred to serum vials either with or without Cr(VI), prepared and incubated as in Example 6. Cr(VI) reduction was monitored as stated in Example 6. Bacterial density was measured by spectrophotometry at 600 nm.

Figure 8:
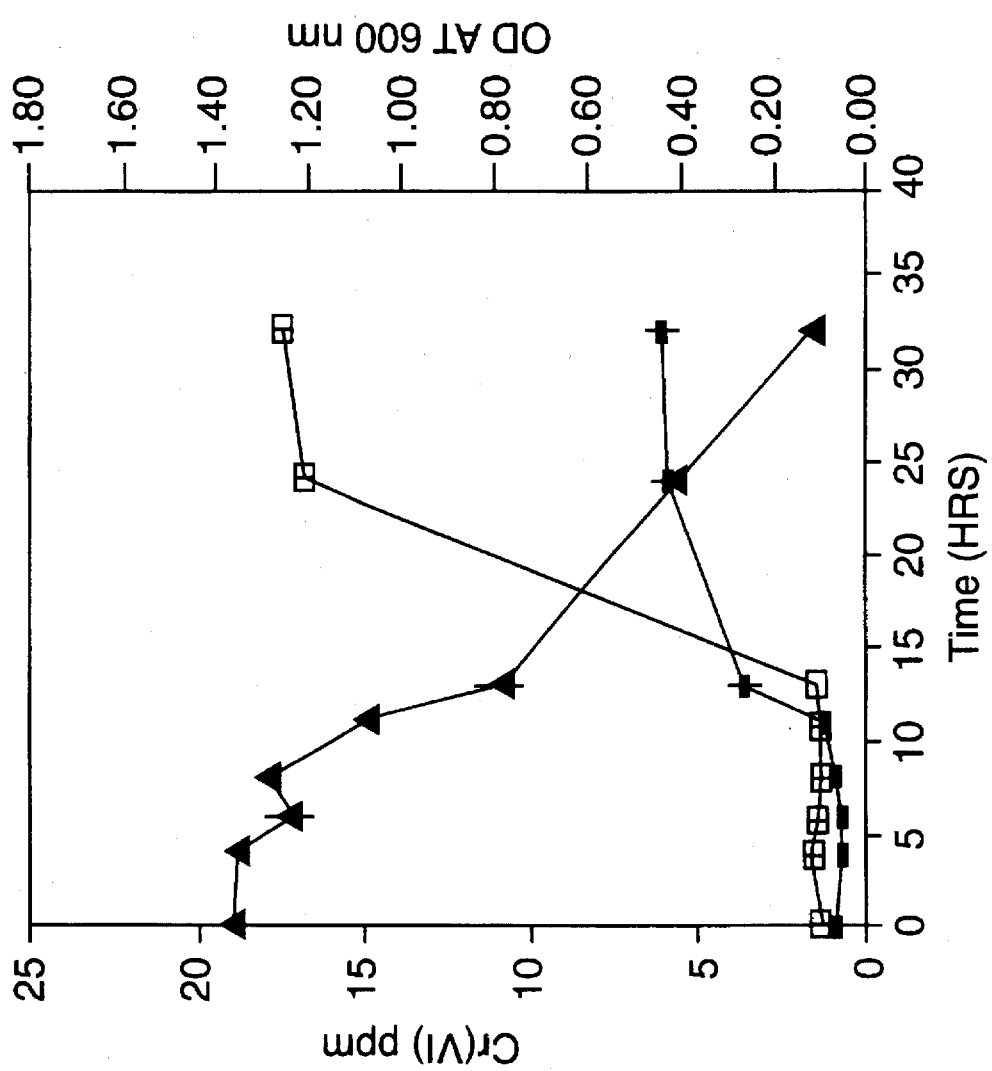
FIG. 8 shows anaerobic Cr(VI) reduction (▲) and bacterial growth after the first transfer of various soil inocula (CAS, RCSM, AG, GSS, and NCSS) with Cr(VI) added (■) or no Cr(VI) added (□).
Figure 9:
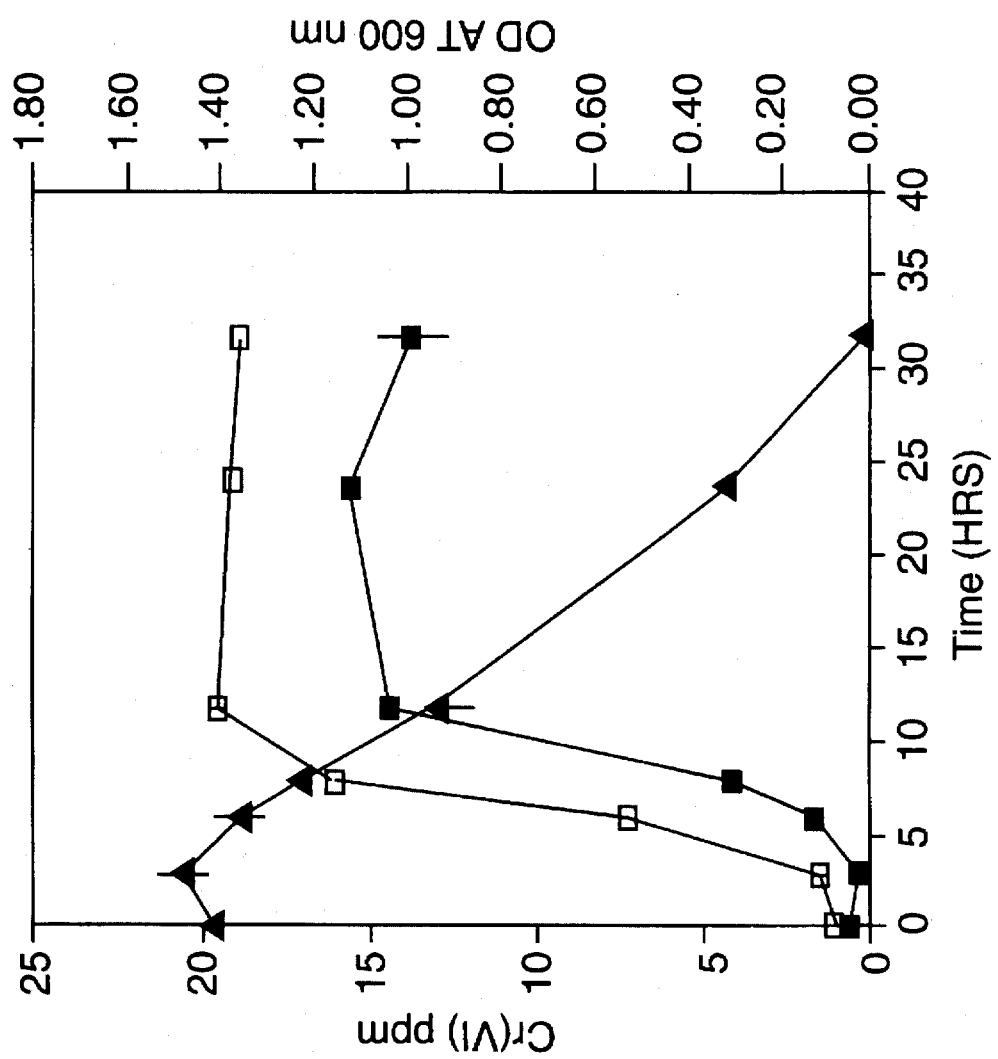
FIG. 9 shows anaerobic Cr(VI) reduction (▲) and bacterial growth after the first transfer of various soil inocula (NCF, VHF, and EDF) with Cr(VI) added (■) or no Cr(VI) added (□).

FIGS. 8 and 9 show that after anaerobic transfer of the soil cultures there was growth inhibition by Cr(VI), although growth was not completely arrested. Cr(VI) reduction coincided with bacterial growth of all soil samples examined. Minimal reduction occurred during the lag phase of growth, with the highest rates of reduction occurring from soils CAS, RCSM, AG, GSS, and NCSS during the log phase of growth (FIG. 8). In the cases of soils NCF, VHF, and EDF (FIG. 9), Cr(VI) reduction rates remained constant throughout log and stationary growth phases. These results are indicative of direct bacterial reduction of Cr(VI) associated with growth.

Example 9

The degree of Cr(VI) reduction related to abiotic reactions with organics and redox conditions was determined for the control cultures of Example 8. Eh was varied (243 to −380 mV) in abiotic controls containing Cr(VI) by adding either air or various amounts of oxygen free nitrogen and hydrogen until the selected Eh was attained.

Figure 10:
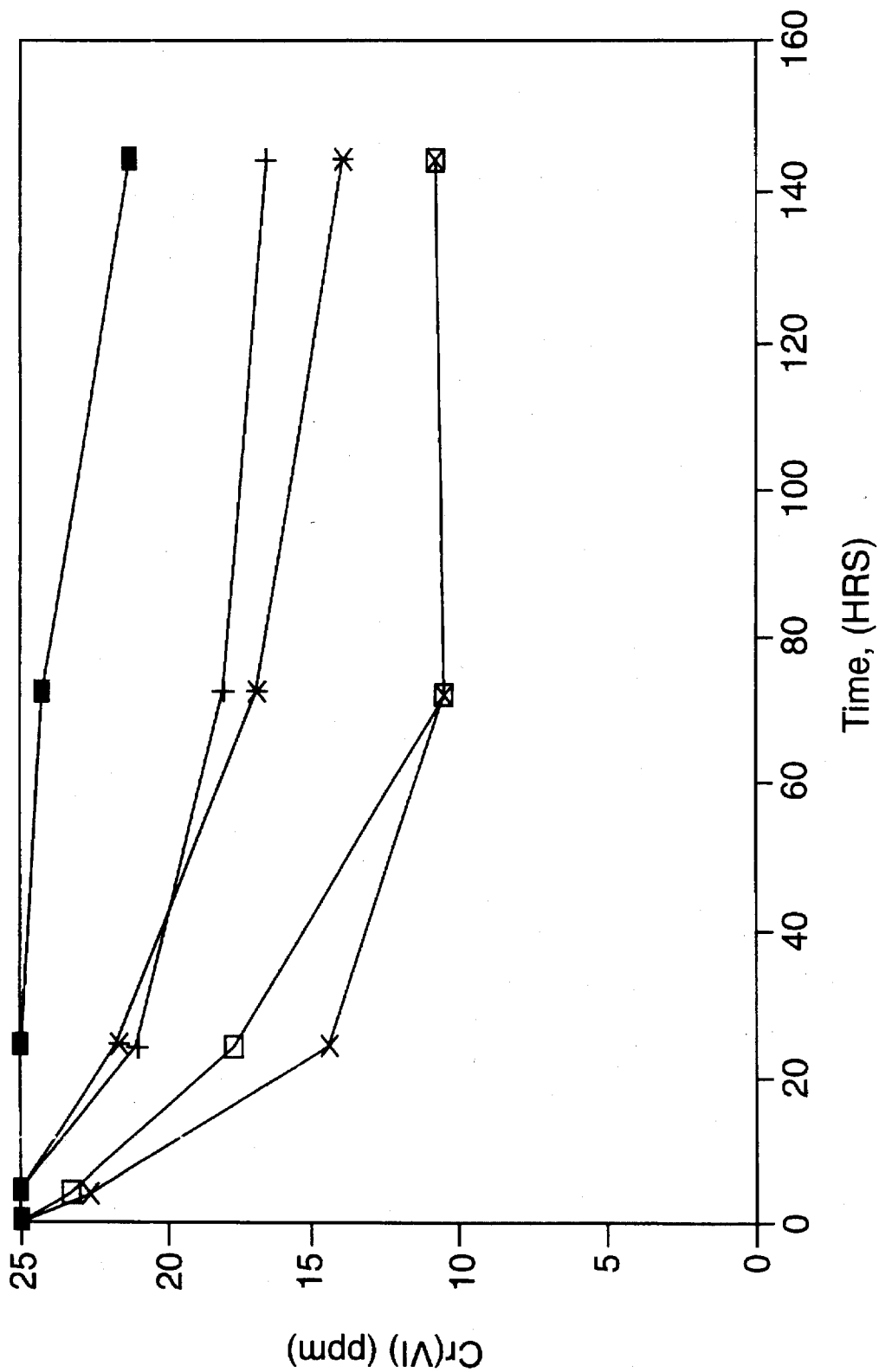
FIG. 10 shows abiotic Cr(VI) reduction as a function of Eh: 243 mV (■); 186 mV (+); 58 mV (*); −128 mV (□); −380 mV (x).

Abiotic Cr(VI) reduction with various Eh values indicate Cr(VI) reduction occurred with time as a function of Eh, with the lower Eh values yielding greater rates and degrees of reduction (FIG. 10). The rates and degree of reduction in these abiotic controls were substantially less than that occurring during bacterial growth (FIGS. 8 and 9), indicating minimal effects of organics on Cr(VI) reduction as Eh values may have decreased during these studies.

Example 10

Bacterial isolates were obtained from the serum vials of Example 6 after Cr(VI) reduction was evident using the spread plate method. Individual isolates were then analyzed to determine Cr(VI) reduction ability using the procedures of Example 6. Pure cultures of Cr(VI) were then analyzed morphologically and physiologically to ascertain the degree of bacterial diversity of anaerobic Cr(VI) reducers in the environment. Physiological tests were conducted at 30° C. using OXY/FERM and ENTEROTUBE (Becton Dickinson Microbiology Systems) test systems. Nitrate reductase analyses were conducted using nitrite test strips (Difco).

These tests permitted assessment of microbial diversity associated with indigenous Cr(VI) reducers. All isolates were Gram negative rods demonstrating physiological characteristics primarily indicative of the Pseudomonadaceae, Vibrionaceae, and Enterobacteriaceae. Only one isolate, from soil sample CAS, did not reduce Cr(VI) to a greater degree than controls. All other isolates recovered did reduce Cr(VI) to a greater extent and at a greater rate than abiotic controls. $H_2S$ production was not detected for any of the isolates and can therefore be discounted as a factor in Cr(VI) reduction from these soil isolates.

We claim:

1. A method of reducing levels of Cr(VI) in a liquid aqueous residue comprising
   (a) providing a consortium of anaerobic Cr(VI) reducing bacteria that use Cr(VI) as a terminal electron acceptor for reducing Cr(VI) to Cr(III), wherein said bacteria are selected by a method comprising
      (I) collecting a soil sample,
      (ii) diluting the soil sample with a sterile aqueous diluent to form a diluted sample,
      (iii) mixing the diluted sample with an effective amount of a bacterial growth nutrient medium and an effective amount of Cr(VI) to form a mixture, and
      (iv) incubating said mixture in the substantial absence of oxygen such that growth of said anaerobic Cr(VI) reducing bacteria is stimulated;
   (b) mixing the liquid aqueous residue with an effective amount of a bacterial growth nutrient medium to form a mixture; and
   (c) contacting the mixture in the substantial absence of oxygen with said consortium of anaerobic Cr(VI) reducing bacteria such that the bacteria use Cr(VI) as a terminal electron acceptor and thereby reduce the Cr(VI) to Cr(III).

2. The method of claim 1 wherein said effective amount of Cr(VI) is about 0.1 to about 25,000 mg/L.

3. The method of claim 2 wherein said effective amount of Cr(VI) is about 10 to about 750 mg/L.

4. The method of claim 3 wherein said effective amount of Cr(VI) is about 50 to about 400 mg/L.

5. The method of claim 1 wherein said incubating step is at a temperature of about 4° C. to about 65° C.

6. The method of claim 5 wherein said incubating step is for a time up to about 48 hours.

7. The method of claim 6 wherein said bacterial growth nutrient medium is a member selected from the group consisting of carbohydrates, amino acids, organic acids, nitrogen sources, and mixtures thereof.

8. The method of claim 7 wherein said nutrient medium is a member selected from the group consisting of molasses, acetic acid and salts thereof, amino acids, casamino acids, urea, and mixtures thereof.

9. The method of claim 8 wherein said incubating step is performed in a bioreactor.

10. The method of claim 9 wherein said bioreactor comprises a solid support.

11. The method of claim 9 wherein said bioreactor comprises a continuously stirred reactor.

12. The method of claim 1 wherein said liquid aqueous residue is a member selected from the group consisting of groundwater, industrial effluent, waste water, soil wash, and mixtures thereof.

13. The method of claim 12 wherein said bacterial growth nutrient medium is a member selected from the group consisting of carbohydrates, amino acids, organic acids, nitrogen sources, and mixtures thereof.

14. The method of claim 13 wherein said nutrient medium is a member selected from the group consisting of molasses, acetic acid and salts thereof, amino acids, casamino acids, urea, and mixtures thereof.

15. The method of claim 14 wherein said contacting step is performed in a bioreactor.

16. The method of claim 15 wherein said bioreactor comprises a solid support.

17. The method of claim 15 wherein said bioreactor comprises a continuously stirred reactor.

18. The method of claim 15 wherein said bioreactor is operated in continuous mode.

19. The method of claim 18 wherein said contacting step is performed at a temperature of about 4° C. to about 65° C.

20. A method of selecting anaerobic Cr(VI) reducing bacteria that use Cr(VI) as a terminal electron acceptor for reducing Cr(VI) to Cr(III) comprising
   (a) collecting a soil sample;
   (b) diluting the soil sample with a sterile aqueous diluent to form a diluted sample;
   (c) mixing the diluted sample with an effective amount of a bacterial growth nutrient medium and an effective amount of Cr(VI) to form a mixture; and
   (d) incubating said mixture in the substantial absence of oxygen such that growth of said anaerobic Cr(VI) reducing bacteria is stimulated.

21. The method of claim 20 wherein said effective amount of Cr(VI) is about 0.1 to about 25,000 mg/L.

22. The method of claim 21 wherein said effective amount of Cr(VI) is about 10 to about 750 mg/L.

23. The method of claim 22 wherein said effective amount of Cr(VI) is about 50 to about 400 mg/L.

24. The method of claim 20 wherein said incubating step is at a temperature of about 4° C. to about 65° C.

25. The method of claim 24 wherein said incubating step is for a time up to about 48 hours.

26. The method of claim 25 wherein said nutrient medium is a member selected from the group consisting of carbohydrates, amino acids, organic acids, nitrogen sources, and mixtures thereof.

27. The method of claim 26 wherein said nutrient medium is a member selected from the group consisting of molasses, acetic acid and salts thereof, amino acids, casamino acids, urea, and mixtures thereof.

28. The method of claim 27 wherein said incubating step is performed in a bioreactor.

29. The method of claim 28 wherein said bioreactor comprises a solid support.

30. The method of claim 28 wherein said bioreactor comprises a continuously stirred reactor.

31. The product produced by the process of claim 30.

32. The product produced by the process of claim 20.

33. A method of in situ bioremediation for reducing the concentration of Cr(VI) in contaminated soil and/or groundwater comprising providing an effective amount of a nutrient medium and maintaining said contaminated soil and/or groundwater in substantial absence of oxygen whereby growth of indigenous Cr(VI) reducing bacteria is stimulated such that said bacteria reduce Cr(VI) to Cr(III).

34. The method of claim 33 wherein said nutrient is a member selected from the group consisting of carbohydrates, amino acids, organic acids, nitrogen sources, and mixtures thereof.

35. The method of claim 34 wherein said nutrient medium is a member selected from the group consisting of molasses, acetic acid and salts thereof, amino acids, casamino acids, urea, and mixtures thereof.

* * * * *